United States Patent [19]
Eriksson et al.

[11] Patent Number: 5,607,918
[45] Date of Patent: Mar. 4, 1997

[54] VASCULAR ENDOTHELIAL GROWTH FACTOR-B AND DNA CODING THEREFOR

[75] Inventors: Ulf Eriksson, Bålsta; Birgitta Olofsson, Sundbyberg, both of Sweden; Kari Alitalo; Katri Pajusola, both of Helsinki, Finland

[73] Assignees: Ludwig Institute for Cancer Research, New York, N.Y.; Helsinki University Licensing Ltd. Oy, University of Helsinki, Finland

[21] Appl. No.: 469,427

[22] Filed: Jun. 6, 1995

Related U.S. Application Data

[63] Continuation-in-part of Ser. No. 397,651, Mar. 1, 1995.
[51] Int. Cl.$^6$ .................... A61K 38/18; C07K 14/475
[52] U.S. Cl. ................................ 514/12; 530/350
[58] Field of Search ................... 530/350; 514/12

[56] References Cited

FOREIGN PATENT DOCUMENTS

WO95/24473  9/1995  WIPO.

OTHER PUBLICATIONS

Klagsburn et al, Ann. Rev. Physiology, 1991, vol. 53: pp. 217–239.

Ferrara et al., J. of Cellular Biochem., 1991, vol. 47: pp. 211–218.

Folkman et al, J. of Biological Chem., Jun., 1992, vol. 267 (16): pp. 10931–10934.

*Primary Examiner*—Mindy Fleisher
*Assistant Examiner*—Terry A. McKelvey
*Attorney, Agent, or Firm*—Evenson, McKeown, Edwards & Lenahan P.L.L.C.

[57] ABSTRACT

VEGF-B polypeptides from the PDGF family of growth factors having the property of promoting mitosis and proliferation of vascular endothelial cells, DNA sequences encoding these polypeptides, pharmaceutical compositions containing them and antibodies which react with them. The VEGF-B polypeptides are useful in stimulating angiogenesis as well as in diagnostic applications.

13 Claims, 6 Drawing Sheets

Figure 1
Deduced amino acid sequence of 1st reading frame of cDNA clone

```
  1                                                                      CG
    Gly Arg Pro Val Val Pro Trp Ile Asp Val Tyr Ala Arg Ala Thr Cys Gln   17
  3 GGA CGC CCA GTG GTG CCA TGG ATA GAC GTT TAT GCA CGT GCC ACA TGC CAG
    Pro Arg Glu Val Val Val Pro Leu Ser Met Glu Leu Met Gly Asn Val Val   34
 55 CCC AGG GAG GTG GTG GTG CCT CTG AGC ATG GAA CTC ATG GGC AAT GTG GTC
    Lys Gln Leu Val Pro Ser Cys Val Thr Val Gln Arg Cys Gly Gly Cys Cys   51
106 AAA CAA CTA GTG CCC AGC TGT GTG ACT GTG CAG CGC TGT GGT GGC TGC TGC
    Pro Asp Asp Gly Leu Glu Cys Val Pro Thr Gly Gln His Gln Val Arg Met   68
157 CCT GAC GAT GGC CTG GAA TGT GTG CCC ACT GGG CAA CAC CAA GTC CGA ATG
    Gln Ile Leu Met Ile Gln Tyr Pro Ser Ser Gln Leu Gly Glu Met Ser Leu   85
208 CAG ATC CTC ATG ATC CAG TAC CCG AGC AGT CAG CTG GGG GAG ATG TCC CTG
    Glu Glu His Ser Gln Cys Glu Cys Arg Pro Lys Lys Lys Arg Arg Val Leu  102
259 GAA GAA CAC AGC CAA TGT GAA TGC AGA CCA AAA AAA AAA AGG AGA GTG CTG
    Stop
310 TGA AGCCAGACAGCCCCAGGATCCTCTGCCCGCCTTGCACCCAGCGCCGTCAACGCCCTGACCCCC
376 GGACCTGCCGCTGCCGCTGCAGACGCCGCCGCTTCCTCCATTGCCAAGGGCGGGGCTTAGAGCTCAA
443 CCCAGACACCTGTAGGTGCCGGAAGCCGCGAAAGTGACAAGCTGCTTTCCAGACTCCACGGGCCCGG
510 CTGCTTTTATGGCCCTGCTTCACAGGGACGAAGAGTGGAGCACAGGCAAACCTCCTCAGTCTGGGAG
577 GTCACTGCCCCAGGACCTGGACCTTTTAGAGAGCTCTCTCGCCATCTTTTATCTCCCAGAGCTGCCA
644 TCTAACAATTGTCAAGGAACCTCATGTCTCACCTCAGGGGCCAGGGTACTCTCTCACTTAACCACCC
711 TGGTCAAGTGAGCATCTTCTGGCTGGCTGTCTCCCCTCACTATGAAAACCCCAAACTTCTACCAATA
778 ACGGGATTTGGGTTCTGTTATGATAACTGTGACACACACACACACTCACACTCTGATAAAAGAGAAC
845 TCTGATAAAAGAGATGGAAGACACTAAAAAAAAAAAAAAAAAA
```

(SEQ ID NOS:1 & 2)

Figure 2
Deduced amino acid sequence of 2nd reading frame of cDNA clone.

```
  1                                                              CGGGACGCC
 10 CAGTGGTGCCATGGATAGACGTTTATGCACGTGCCACATGCCAGCCCAGGGAGGTGGTGGTGCCTCT
 77 GAGCATGGAACTCATGGGCAATGTGGTCAAACAACTAGTGCCCAGCTGTGTGACTGTGCAGCGCTGT
144 GGTGGCTGCTGCCCTGACGATGGCCTGGAATGTGTGCCCACTGGGCAACACCAAGTCCGAATGCAGA
211 TCCTCATGATCCAGTACCCGAGCAGTCAGCTGGGGGAGATGTCCCTGGAAGAACACAGCCAATGTGA
                                            Lys Pro Asp Ser Pro Arg    7
278 ATG CAG ACC AAA AAA AAA AAG GAG AGT GCT GTG AAG CCA GAC AGC CCC AGG
    Ile Leu Cys Pro Pro Cys Thr Gln Arg Arg Gln Arg Pro Asp Pro Arg Thr  24
330 ATC CTC TGC CCG CCT TGC ACC CAG CGC CGT CAA CGC CCT GAC CCC CGG ACC
    Cys Arg Cys Arg Cys Arg Arg Arg Arg Phe Leu His Cys Gln Gly Arg Gly  41
381 TGC CGC TGC CGC TGC AGA CGC CGC CGC TTC CTC CAT TGC CAA GGG CGG GGC
    Leu Glu Leu Asn Pro Asp Thr Cys Arg Cys Arg Lys Pro Arg Lys Stop     56
432 TTA GAG CTC AAC CCA GAC ACC TGT AGG TGC CGG AAG CCG CGA AAG TGA CAA
483 GCTGCTTTCCAGACTCCACGGGCCCGGCTGCTTTTATGGCCCTGCTTCACAGGGACGAAGAGTGGAG
550 CACAGGCAAACCTCCTCAGTCTGGGAGGTCACTGCCCCAGGACCTGGACCTTTTAGAGAGCTCTCTC
617 GCCATCTTTTATCTCCCAGAGCTGCCATCTAACAATTGTCAAGGAACCTCATGTCTCACCTCAGGGG
684 CCAGGGTACTCTCTCACTTAACCACCCTGGTCAAGTGAGCATCTTCTGGCTGGCTGTCTCCCCTCAC
751 TATGAAAACCCCAAACTTCTACCAATAACGGGATTTGGGTTCTGTTATGATAACTGTGACACACACA
816 CACACTCACACTCTGATAAAAGAGAACTCTGATAAAAGAGATGGAAGACACTAAAAAAAAAAAAAAA
885 AAA
```

(SEQ ID NOS:1 & 3)

Figure 3
Coding region of clones encoding VEGF-B₁₆₆

```
GAGCCCCCTG CTCCGTCGCC TGCTGCTTGT TGCACTGCTG CAGCTGGCTC
GCACCCAGGC CCCTGTGTCC CAGTTTGATG GCCCCAGCCA CCAGAAGAAA
GTGGTGCCAT GGATAGACGT TTATGCACGT GCCACATGCC AGCCCAGGGA
GGTGGTGGTG CCTCTGAGCA TGGAACTCAT GGGCAATGTG GTCAAACAAC
TAGTGCCCAG CTGTGTGACT GTGCAGCGCT GTGGTGGCTG CTGCCCTGAC
GATGGCCTGG AATGTGTGCC CACTGGGCAA CACCAAGTCC GAATGCAGAT
CCTCATGATC CAGTACCCGA GCAGTCAGCT GGGGGAGATG TCCCTGGAAG
AACACAGCCA ATGTGAATGC AGACCAAAAA AAAAGGAGAG TGCTGTGAAG
CCAGACAGCC CCAGGATCCT CTGCCCGCCT TGCACCCAGC GCCGTCAACG
CCCTGACCCC CGGACCTGCC GCTGCCGCTG CAGACGCCGC CGCTTCCTCC
ATTGCCAAGG GCGGGGCTTA GAGCTCAACC CAGACACCTG TAGGTGCCGG
AAGCCGCGAA AGTGA
(SEQ ID NO:4)
```

Figure 4
Deduced amino acid sequence of VEGF-B₁₆₆

```
MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
ILMIQYPSSQ LGEMSLEEHS QCECRPKKKE SAVKPDSPRI LCPPCTQRRQ
RPDPRTCRCR CRRRRFLHCQ GRGLELNPDT CRCRKPRK
(SEQ ID NO:5)
```

Figure 5
Coding sequence of clone encoding VEGF-B₁₇₃

```
ACCATGAGCC CCTGCTCCG TCGCCTGCTG CTTGTTGCAC TGCTGCAGCT
GGCTCGCACC CAGGCCCCTG TGTCCCAGTT TGATGGCCCC AGCCACCAGA
AGAAAGTGGT GCCATGGATA GACGTTTATG CACGTGCCAC ATGCCAGCCC
AGGGAGGTGG TGGTGCCTCT GAGCATGGAA CTCATGGGCA ATGTGGTCAA
ACAACTAGTG CCCAGCTGTG TGACTGTGCA GCGCTGTGGT GGCTGCTGCC
CTGACGATGG CCTGGAATGT GTGCCCACTG GCAACACCA AGTCCGAATG
CAGGTACCAG GGCTATGGG TCAGATCCTC ATGATCCAGT ACCCGAGCAG
TCAGCTGGGG GAGATGTCCC TGGAAGAACA CAGCCAATGT GAATGCAGAC
CAAAAAAAA GGAGAGTGCT GTGAAGCCAG ACAGCCCCAG GATCCTCTGC
CCGCCTTGCA CCCAGCGCCG TCAACGCCCT GACCCCGGA CCTGCCGCTG
CCGCTGCAGA CGCCGCCGCT TCCTCCATTG CCAAGGGCGG GGCTTAGAGC
TCAACCCAGA CACCTGTAGG TGCCGGAAGC CGCGAAAGTG A
(SEQ ID NO:6)
```

Figure 6
Deduced amino acid sequence of VEGF-B$_{173}$

MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
VPGPMGQILM IQYPSSQLGE MSLEEHSQCE CRPKKKESAV KPDSPRILCP
PCTQRRQRPD PRTCRCRCRR RRFLHCQGRG LELNPDTCRC RKPRK
(SEQ ID NO:7)

Figure 7
Coding region of cDNA encoding VEGF-B$_{112}$

ACCATGAGCC CCCTGCTCCG TCGCCTGCTG CTTGTTGCAC TGCTGCAGCT
GGCTCGCACC CAGGCCCCTG TGTCCCAGTT TGATGGCCCC AGCCACCAGA
AGAAAGTGGT GCCATGGATA GACGTTTATG CACGTGCCAC ATGCCAGCCC
AGGGAGGTGG TGGTGCCTCT GAGCATGGAA CTCATGGGCA ATGTGGTCAA
ACAACTAGTG CCCAGCTGTG TGACTGTGCA GCGCTGTGGT GGCTGCTGCC
CTGACGATGG CCTGGAATGT GTGCCCACTG GCAACACCA AGTCCGAATG
CAGATCCTCA TGATCCAGTA CCCGAGCAGT CAGCTGGGGG AGATGTCCCT
GGAAGAACAC AGCCAATGTG AATGCAGACC AAAAAAAAAA AGGAGAGTGC
TGTGA
(SEQ ID NO:8)

Figure 8
Deduced amino acid sequence of VEGF-B$_{112}$

MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
ILMIQYPSSQ LGEMSLEEHS QCECRPKKR RVL
(SEQ ID NO:9)

Figure 9
Amino acid sequence alignments of PDGF A and B, PlGF,
VEGF₁₆₅ and VEGF-B₁₆₆

```
            1                                                        50
PDGF-A    .MRTWACLLL  LGCGYLAHAL  AEEAEIPREL  IERLARSQIH  SIRDLQRLLE
PDGF-B    MNRCWA.LFL  PLCCYLRLVS  AEGDPIPEEL  YEMLSDHSIR  SFDDLQRLLH
PLGF      ..........  ..........  ..........  ..........  ....MPVMRL
VEGF      ..........  ..........  ..........  ..........  .......MNF
VEGF-B    ..........  ..........  ..........  ..........  .......MSP 51                                                       100
PDGF-A    IDSVGAEDA.  LETSL.RAHG  SHAINHVPEK  RPVPIRRKRS  IEEAIPAVCK
PDGF-B    RDSVDEDGAE  LDLNMTRAHS  GVELESSSRG  RR.SLGSLAA  AEPAVIAECK
PLGF      FPCFLQLLAG  LALPAVPPQQ  WALSAGNGSS  EV...EVVPF  QEVWGRSYCR
VEGF      LLSWVHWTLA  LLLYLHHAKW  SQAAPTTEGE  QKSHEVIKF.  .DVYQRSYCR
VEGF-B    LLS.....SL  LLVALMQLAR  TQAPVSQFDG  PSHQKKVVPW  IDVYARATCQ 101                                                      150
PDGF-A    TRTVIYEIPR  SQVDPTSANF  LIWPPCVEVK  RCTGCCNTSS  VKCQPSRVHH
PDGF-B    TRTEVFQISR  NLIDRTNANF  LVWPPCVEVQ  RCSGCCNNRN  VQCRASQVQM
PLGF      ALERLVDVVS  EYPS..EVEH  MFSPSCVSLL  RCTGCCGDEN  LHCVPVETAN
VEGF-A    PIETLVDIFQ  EYPD..EIEY  IFKPSCVPLM  RCAGCCNDEA  LECVPTSESN
VEGF-B    PREVVVPLSM  ELMG..NVVK  QLVPSCVTVQ  RCGGCCPDDG  LECVPTAEHQ 151                                                      200
PDGF-A    RSVKVAKVEY  VRKKPKLKEV  QVRLEEHLEC  ACAT......  ....SNLNPD
PDGF-B    RPVQVRKIEI  VRKKPIFKKA  TVTLEDHLAC  KCETIVTPRP  VTRSPGTSRE
PLGF      VTMQLLKIRS  GDRPSY...V  ELTFSQHVRC  EC.....RPL  REK...MKPE
VEGF      ITMQIMRIKP  HQSQHI...E  RMSFLQHSRC  EC.....RPK  KDR...TKPE
VEGF-B    VRMQILMIQY  PSSQ.L...G  EMSLEEHSQC  EC.....RPK  KKESA.VKPD 201                                                      250
PDGF-A    HREEETDVR.  ..........  ..........  ..........  ..........
PDGF-B    QRAKTPQARV  TIRTVRIRRP  PKGKHRKFKH  THDKAALKET  LGA.......
PLGF      RCGDAVPRR.  ..........  ..........  ..........  ..........
VEGF      ...NHCEPCS  ERRKHLFVQD  PQTCKCSCKN  TDS.RCKARQ  LELNERTCRC
VEGF-B    SPRILPPCT   QRRQR...PD  PRTCRCRCRR  RRFLHCQGRG  LELNPDTCRC

251
PDGF-A    ..       (SEQ ID NO:12)
PDGF-B    ..       (SEQ ID NO:13)
PLGF      ..       (SEQ ID NO:14)
VEGF-A    DKPRR    (SEQ ID NO:15)
VEGF-B    RKPRK    (SEQ ID NO: 5)
```

Figure 10
Coding region of clone H.1 encoding human VEGF-B$_{166}$

```
ACCATGAGCC CTCTGCTCCG CCGCCTGCTG CTCGCCGCAC TCCTGCAGCT
GGCCCCCGCC CAGGCCCCTG TCTCCCAGCC TGATGCCCCT GGCCACCAGA
GGAAAGTGGT GTCATGGATA GATGTGTATA CTCGCGCTAC CTGCCAGCCC
CGGGAGGTGG TGGTGCCCTT GACTGTGGAG CTCATGGGCA CCGTGGCCAA
ACAGCTGGTG CCCAGCTGCG TGACTGTGCA GCGCTGTGGT GGCTGCTGCC
CTGACGATGG CCTGGAGTGT GTGCCCACTG GCAGCACCA AGTCCGGATG
CAGATCCTCA TGATCCGGTA CCCGAGCAGT CAGCTGGGGG AGATGTCCCT
GGAAGAACAC AGCCAGTGTG AATGCAGACC TAAAAAAAG GACAGTGCTG
TGAAGCCAGA CAGCCCCAGG CCCCTCTGCC CACGCTGCAC CCAGCACCAC
CAGCGCCCTG ACCCCGGAC CTGCCGCTGC CGCTGCCGAC GCCGCAGCTT
CCTCCGTTGC CAAGGGCGGG GCTTAGAGCT CAACCCAGAC ACCTGCAGGT
GCCGGAAGCT GCGAAGGTGA
(SEQ ID NO:10)
```

Figure 11
Deduced amino acid sequence of human VEGF-B$_{166}$

```
MSPLLRRLLL AALLQLAPAQ APVSQPDAPG HQRKVVSWID VYTRATCQPR
EVVVPLTVEL MGTVAKQLVP SCVTVQRCGG CCPDDGLECV PTGQHQVRMQ
ILMIRYPSSQ LGEMSLEEHS QCECRPKKKD SAVKPDSPRP LCPRCTQHHQ
RPDPRTCRCR CRRRSFLRCQ GRGLELNPDT CRCRKLRR
(SEQ ID NO:11)
```

Figure 12
Amino acid sequence alignment of mouse (upper) and human (lower) VEGF-B$_{166}$

```
1                                                                    50
:                                                                     :
MSPLLRRLLL VALLQLARTQ APVSQFDGPS HQKKVVPWID VYARATCQPR
|||||||||| *|||||||**| |||||*|*|* ||*|||*||| ||*||||||||
MSPLLRRLLL AALLQLAPAQ APVSQPDAPG HQRKVVSWID VYTRATCQPR 51                                                                  100
:                                                                     :
EVVVPLSMEL MGNVVKQLVP SCVTVQRCGG CCPDDGLECV PTGQHQVRMQ
||||||**|| ||*|*||||| |||||||||| |||||||||| ||||||||||
EVVVPLTVEL MGTVAKQLVP SCVTVQRCGG CCPDDGLECV PTGQHQVRMQ 101                                                                 150
:                                                                     :
ILMIQYPSSQ LGEMSLEEHS QCECRPKKKE SAVKPDSPRI LCPPCTQRRQ
||||*||||| |||||||||| |||||||||* |||||||||* |||*|||**|
ILMIRYPSSQ LGEMSLEEHS QCECRPKKKD SAVKPDSPRP LCPRCTQHHQ 151                                          188
:                                             :
RPDPRTCRCR CRRRRFLHCQ GRGLELNPDT CRCRKPRK    (SEQ ID NO: 5)
|||||||||| ||||*||*|| |||||||||| ||||*|*
RPDPRTCRCR CRRRSFLRCQ GRGLELNPDT CRCRKLRR    (SEQ ID NO:11)
```

VASCULAR ENDOTHELIAL GROWTH FACTOR-B AND DNA CODING THEREFOR

CROSS-REFERENCE TO RELATED APPLICATION

This application is a continuation-in-part of copending application Ser. No. 08/397,651, filed Mar. 1, 1995.

BACKGROUND OF THE INVENTION

Angiogenesis, or the proliferation of new capillary blood vessels, is a fundamental process necessary for normal growth and development of tissues. It is a prerequisite for the development and differentiation of the vascular tree, as well as for a wide variety of fundamental physiological processes including embryogenesis, somatic growth, tissue and organ repair and regeneration, cyclical growth of the corpus luteum and endometrium, and development and differentiation of the nervous system. In the female reproductive system, angiogenesis occurs in the follicle during its development, in the corpus luteum following ovulation and in the placenta to establish and maintain pregnancy. Angiogenesis additionally occurs as part of the body's repair processes, e.g. in the healing of wounds and fractures. Angiogenesis is also a factor in tumor growth, since a tumor must continuously stimulate growth of new capillary blood vessels in order to grow.

Capillary blood vessels consist of endothelial cells and pericytes. These two cell types carry all of the genetic information to form tubes, branches and entire capillary networks. Specific angiogenic molecules can initiate this process. In view of the physiological importance of angiogenesis, much effort has been devoted to the isolation, characterization and purification of factors that can stimulate angiogenesis, and a number of polypeptides which stimulate angiogenesis have been purified and characterized as to their molecular, biochemical and biological properties. For reviews of such angiogenesis regulators, see Klagsbrun et al., "Regulators of Angiogenesis", *Ann. Rev. Physiol.*, 53:217–39 (1991); and Folkman et al., "Angiogenesis," *J. Biol. Chem.*, 267:10931–934 (1992).

One such growth factor, which is highly specific as a mitogen for vascular endothelial cells, is termed vascular endothelial growth factor (VEGF). See Ferrara et al., "The Vascular Endothelial Growth Factor Family of Polypeptides," *J. Cellular Biochem.*, 47:211–218 (1991); Connolly, "Vascular Permeability Factor: A Unique Regulator of Blood Vessel Function," *J. Cellular Biochem.*, 47:219–223 (1991). VEGF is a potent vasoactive protein that has been detected in media conditioned by a number of cell lines including bovine pituitary follicular cells. VEGF is a glycosylated cationic 46–48 kD dimer made up of two 24 kD subunits. It is inactivated by sulfhydryl reducing agents, resistant to acidic pH and to heating, and binds to immobilized heparin. VEGF is sometimes referred to as vascular permeability factor (VPF) because it increases fluid leakage from blood vessels following intradermal injection. It also has been called by the name vasculotropin.

Four different molecular species of VEGF have been detected. The 165 amino acid species has a molecular weight of approximately 46 kD and is the predominant molecular form found in normal cells and tissues. A less abundant, shorter form with a deletion of 44 amino acids between positions 116 and 159 ($VEGF_{121}$), a longer form with an insertion of 24 highly basic residues in position 116 ($VEGF_{189}$), and another longer form with an insertion of 41 amino acids ($VEGF_{206}$), which includes the 24 amino acid insertion found in $VEGF_{189}$, are also known. $VEGF_{121}$ and $VEGF_{165}$ are soluble proteins. $VEGF_{189}$ and $VEGF_{206}$ appear to be mostly cell-associated. All of the versions of VGEF are biologically active. For example, each of the species when applied intradermally is able to induce extravasation of Evans blue.

The various species of VEGF are encoded by the same gene and arise from alternative splicing of messenger RNA. This conclusion is supported by Southern blot analysis of human genomic DNA, which shows that the restriction pattern is identical using either a probe for $VEGF_{165}$ or one which contains the insertion in $VEGF_{206}$. Analysis of genomic clones in the area of putative mRNA splicing also shows an intron/exon structure consistent with alternative splicing.

Analysis of the nucleotide sequence of the VEGF gene indicates that VEGF is a member of the platelet-derived growth factor (PDGF) family. The amino acid sequence of VEGF exhibits approximately 20% homology to the sequences of the A and B chains of PDGF, as well as complete conservation of the eight cysteine residues found in both mature PDGF chains. $VEGF_{165}$, $VEGF_{189}$ and $VEGF_{206}$ also contain eight additional cysteine residues within the carboxy-terminal region. The amino-terminal sequence of VEGF is preceded by 26 amino acids corresponding to a typical signal sequence. The mature protein is generated directly following signal sequence cleavage without any intervening prosequence. The existence of a potential glycosylation site at $Asn^{74}$ is consistent with other evidence that VEGF is a glycoprotein, but the polypeptide has been reported to exist in both glycosylated and deglycosylated species.

Like other cytokines, VEGF can have diverse effects that depend on the specific biological context in which it is found. VEGF is a potent endothelial cell mitogen and directly contributes to induction of angiogenesis in vivo by promoting endothelial cell growth during normal development or during wound healing. A most striking property of VEGF is its specificity. It is mitogenic in vitro at 1 ng/ml for capillary and human umbilical vein endothelial cells, but not for adrenal cortex cells, corneal or lens epithelial cells, vascular smooth muscle cells, corneal endothelial cells, granulosa cells, keratinocytes, BHK-21 fibroblasts, 3T3 cells, rat embryo fibroblasts, human placental fibroblasts and human sarcoma cells. The target cell specificity of VEGF is thus restricted to vascular endothelial cells. VEGF can trigger the entire sequence of events leading to angiogenesis and stimulates angiogenesis in vivo in the cornea and in a healing bone graft model. It is able to stimulate the proliferation of endothelial cells isolated from both small and large vessels. Expression of VEGF mRNA is temporally and spatially related to the physiological proliferation of capillary blood vessels in the ovarian corpus luteum or in the developing brain. VEGF expression is triggered by hypoxemia so that endothelial cell proliferation and angiogenesis appear to be especially stimulated in ischemic areas. VEGF is also a potent chemoattractant for monocytes. In addition, VEGF induces plasminogen activator and plasminogen activator inhibitor in endothelial cells.

Tumor cells release angiogenic molecules such as VEGF, and monoclonal antibodies to VEGF have been shown to inhibit the growth of certain types of tumor such as rhabdomyosarcoma. See Kim et al., "Inhibition of Vascular Endothelial Growth Factor-Induced Angiogenesis Suppresses Tumor Growth in vivo," *Nature*, 362:841–844 (1993). This suggests that blocking VEGF action is of

3 potential therapeutic significance in treating tumors in general, and highly-vascularized, aggressive tumors in particular.

SUMMARY OF THE INVENTION

It is an object of the invention to provide a new growth factor having the property of promoting proliferation of endothelial cells.

Another object of the invention is to provide isolated DNA sequences which encode a new growth factor which promotes proliferation of endothelial cells.

It is also an object of the invention to provide new products which may be useful in diagnostic and/or therapeutic applications.

These and other objects are achieved in accordance with the present invention by providing an isolated DNA which codes for a protein having the property of promoting proliferation of endothelial cells or mesodermal cells, the DNA being selected from the group consisting of the DNA of FIGS. 1 and 2 (SEQ ID NO:1), the DNA of FIG. 3 (SEQ ID NO:4), the DNA of FIG. 5 (SEQ ID NO:6); the DNA of FIG. 7 (SEQ ID NO:8), and DNA's which hybridize under stringent conditions with at least one of the foregoing DNA sequences.

In accordance with further aspects of the invention, the objects are also achieved by providing a protein having the property of promoting proliferation of endothelial cells or mesodermal cells, which protein comprises a sequence of amino acids substantially corresponding to an amino acid sequence selected from the group consisting of the amino acid sequence of FIG. 1 (SEQ ID NO:2), the amino acid sequence of FIG. 2 (SEQ ID NO:3), the amino acid sequence of FIG. 4 (SEQ ID NO:5), the amino acid sequence of FIG. 6 (SEQ ID NO:7), and the amino acid sequence of FIG. 8 (SEQ ID NO:9); and by providing pharmaceutical preparations which comprise such proteins; and by providing antibodies which react with such proteins.

Clinical applications of the invention include diagnostic applications, acceleration of angiogenesis in wound healing, and inhibition of angiogenesis. Quantitation of VEGF-B in cancer biopsy specimens may be useful as an indicator of future metastatic risk. Topical application of VEGF-B preparations to chronic wounds may accelerate angiogenesis and wound healing.

BRIEF DESCRIPTION OF THE DRAWINGS

FIG. 1 shows the nucleotide sequence of the (partial) cDNA clone of VEGF-B (SEQ ID NO: 1) and the amino acid sequence of the protein segment (SEQ ID NO:2) coded by the first reading frame of the cDNA;

FIG. 2 repeats the nucleotide sequence of the (partial) cDNA clone of VEGF-B (SEQ ID NO:1) and the amino acid sequence of the protein segment (SEQ ID NO:3) coded by the second reading frame of the cDNA;

FIG. 3 shows the nucleotide sequence of the coding region of a full length cDNA clone of VEGF-$B_{166}$ (SEQ ID NO:4);

FIG. 4 shows the amino acid sequence of VEGF-$B_{166}$ (SEQ ID NO:5);

FIG. 5 shows the nucleotide sequence of the coding region of a cDNA clone of VEGF-$B_{173}$ (SEQ ID NO:6);

FIG. 6 shows the amino acid sequence of VEGF-$B_{173}$ (SEQ ID NO:7);

4

FIG. 7 shows the nucleotide sequence of a cDNA clone of VEGF-$B_{112}$ (SEQ ID NO: 8);

FIG. 8 shows the amino acid sequence of VEGF-$B_{112}$ (SEQ ID NO:9);

FIG. 9 shows a comparison of the amino acid sequences of PDGF-A (SEQ ID NO:12) PDGF-B (SEQ IN NO:13) PlGF (SEQ ID NO:14) VEGF (SEQ ID NO:15) and VEGF-B (SEQ ID NO:5).

FIG. 10 shows the nucleotide sequence of a clone of human VEGF-$B_{166}$ (SEQ ID NO: 10);

FIG. 11 shows the amino acid sequence of human VEGF-$B_{166}$ (SEQ ID NO:11); and FIG. 12 shows a comparison of the sequences of murine (SEQ ID NO: 5) and human (SEQ ID NO:11) VEGF-$B_{166}$.

DETAILED DESCRIPTION OF PREFERRED EMBODIMENTS

The present invention thus is directed to new vascular endothelial growth factors, hereinafter referred to as VEGF-B growth factors, which share the angiogenic and other properties of VEGF, but which are distributed and expressed in tissues differently from VEGF.

VEGF-B growth factors are members of the family of platelet derived growth factors and are a growth factors which promote mitosis and proliferation of vascular endothelial cells and/or mesodermal cells. They are produced by expression of DNA sequences which correspond to, or which are hybridizable under stringent conditions with, any one of the DNA sequences depicted in FIGS. 1 and 2 (SEQ ID NO:1), FIG. 3 (SEQ ID NO:4), FIG. 5 (SEQ ID NO:6) or FIG. 7 (SEQ ID NO:8). It is intended to include within the scope of the invention all angiogenic proteins encoded by DNA sequences which hybridize under stringent conditions to any one of the foregoing DNA sequences. Suitable hybridization conditions include, for example, 50% formamide, 5× SSPE buffer, 5× Denhardts solution, 0.5% SDS and 100 μg/ml of salmon sperm DNA at 42° C. overnight, followed by washing 2×30 minutes in 2× SSC at 55° C.

The invention is also directed to an isolated and/or purified DNA which corresponds to, or which hybridizes under stringent conditions with, any one of the foregoing DNA sequences.

In a further aspect, the invention is directed to antibodies of VEGF-B growth factors, and particularly to monoclonal antibodies.

VEGF-B proteins are believed to interact with protein tyrosine kinase growth factor receptors. Details of such receptors are known in the art [See e.g. Wilks, A. F., "Protein Tyrosine Kinase Growth Factor Receptors and Their Ligands in Development, Differentiation, and Cancer," *Adv. Cancer Res.*, 60:43–73 (1993)].

Various adult mouse tissues were tested for expression of transcripts corresponding to VEGF-B by Northern blotting. The size of the mRNA was 1.3–1.4 kb. A mouse multiple tissue Northern blot (MTN, Clontech) was probed with the 0.89 kb Sal1-Not1 fragment derived from the pPC67 yeast expression vectors described above. The probe was labelled with $^{32}$P-dCTP using random priming (specific activity $10^8$–$10^9$ cpm/μg of DNA). The blot was hybridized overnight at 42° C. using 50% formamide, 5× SSPE buffer, 2% SDS, 10× Denhardts solution, 100 μg/ml salmon sperm DNA and 1×$10^6$ cpm of the labelled probe/ml. The blot was washed at room temperature for 2×30 min in 2× SSC containing 0.05% SDS and then for 2×20 min at 52° C. in 0.1× SSC containing 0.1% SDS. The blot was then exposed at −70° C. for three days using intensifying screens. Kodak XAR film was used. The relative expression levels as determined by visual examinations of the film are listed in the following table:

TABLE 1

Distribution of VEGF-B Transcripts in the Adult Mouse

| Tissue | Relative Expression Level |
| --- | --- |
| Heart | +++++ |
| Brain | +++ |
| Spleen | (+) |
| Lung | ++ |
| Liver | + |
| Skeletal Muscle | ++++ |
| Kidney | +++ |
| Testis | (+) |

+++++ = very strong expression;
++++ = strong expression;
+++ = moderate expression;
++ = rather weak expression;
+ = weak expression;
(+) = very weak expression.

A human multiple tissue Northern blot (MNT) from Clontech was probed using the murine partial cDNA to determine relative VEGF-B expression levels in various human tissues. The size of the transcript was 1.3–1.4 kb. The conditions were identical to those used for the mouse Northern blot described above. The relative VEGF-B transcript levels for the human Northern blot are listed in the following Table 2. For comparison purposes, Table 2 also lists relative expression level data from the literature for VEGF in various mammalian systems.

TABLE 2

| | Relative Expression Levels | | | |
| --- | --- | --- | --- | --- |
| | VEGF-B (Northern blot) | VEGF (from literature) | | |
| Tissues | human | human | murine | guinea pig |
| heart | +++++ | ++ | +++ | +++ |
| brain | + | | + | + |
| placenta | + | | | |
| lung | + | ++++ | | ++ |
| liver | (+) | ++ | (+) | + |
| skeletal muscle | ++++ | | +++ | + |
| kidney | + | ++ | + | ++ |
| pancreas | +++ | | | |
| spleen | ++ | | − | + |
| thymus | + | | − | |
| prostate | +++ | | | |
| testis | ++ | | | (+) |
| ovary | +++ | | | − |
| small intestine | ++ | | | |
| colon | +++ | | | |
| peripheral blood leucocytes | + | | | |

From a comparison of Table 1 and Table 2 it can be seen that mouse and human tissue expression levels of VEGF-B transcripts are relatively similar with the highest expression levels being found in heart and skeletal muscle. Significant differences may be seen in brain and kidney tissue. It should also be noted that tissues containing a large proportion of epithelial cells, such as prostate, pancreas and colon from which some of the most common human tumors originate, express relatively high levels of VEGF-B.

A comparison of the relative expression levels of VEGF and VEGF-B in human tissues shows some striking differences. VEGF is expressed rather weakly by human heart tissue, but VEGF-B is very strongly expressed by the same tissue. On the other hand, VEGF is strongly expressed by human lung tissue, but VEGF-B is only weakly expressed by human lung tissue. In a similar vein, human liver tissue expresses VEGF at a moderate level, but VEGF-B is expressed only very weakly. These data evidence that despite their general similarities, the actions of VEGF and VEGF-B are not completely identical.

EXAMPLE 1

Partial cDNA clone with two reading frames.

A partial cDNA clone encoding murine VEGF-B was identified as follows. A cDNA library (E 14.5) derived from poly A+ mRNA isolated from 14.5 day old mouse embryos [Chevray P. and Nathans D., "Protein interaction cloning in yeast: Identification of mammalian proteins that react with the leucine zipper of Jun, " Proc. Natl. Acad. Sci. USA, 89:5789–93 (1992)] was screened for cellular proteins which potentially might interact with cellular retinoic acid-binding protein type 1 (CRABP-I) using a yeast two-hybrid interaction trap screening technique as described by Gyuris J., Golemis E., Chertkov H. and Brent R., "Cdi1, a Human G1 and S Phase Protein Phosphatase That Associates with Cdk2, " Cell, 75:791–803 (1993). This screening technique involves a fusion protein that contains a binding domain and that is known to be transcriptionally inert (the "bait"); reporter genes that have no basal transcription and that are bound by the bait; and an expression library which encodes proteins expressed as chimeras and whose amino termini contain an activation domain and other useful moieties (the "prey"). The screened library was a plasmid library in the yeast expression vector pPC67 obtained from Dr. Pierre Chevray of the Johns Hopkins University, School of Medicine, 725 North Wolfe St., Baltimore, Md. 21205. A positive cDNA clone (pcif-2) was recovered from the screening. The positive clone was sequenced using well known, conventional techniques and found to encode a protein highly homologous to VEGF and the other members of the PDGF family of growth factors. The 890 base pair SalI-NotI insert in the plasmid pPC67 was cloned into pBluescript and fully sequenced using T7 and T3 vector primers together with internal primers. The plasmid pBluescript is commercially available from Stratagene Inc., LaJolla, Calif. The cDNA insert was found to be 886 base pairs long and to encode two polypeptides in different reading frames which were homologous to the N-terminal end and the C-terminal end, respectively, of VEGF. This novel growth factor is referred to hereinafter as VEGF-B. The clone is partial and lacks several amino acids in the amino terminal region and the entire signal sequence.

FIG. 1 shows the nucleotide sequence (SEQ ID NO:1) of this partial cDNA clone of VEGF-B and the amino acid sequence (SEQ ID NO:2) encoded in the first reading frame thereof. The DNA sequence of FIG. 1 was obtained by conventional sequencing of a clone (pcif-2) in the yeast expression vector pPC67. The clone comprised 886 base pairs and encoded a part of murine VEGF-B.

The isolated cDNA sequence will hybridize with the mammalian genomic DNA, e.g. either murine or human, which contains the VEGF-B gene. In addition to the coding sequence, the genomic DNA will contain one or more promoter sequence(s) which give and direct expression of VEGF-B in one or more specific tissues. Thus the coding sequence of VEGF-B may be linked to an endothelial specific promoter which is specific to a certain type or types of tissue.

The nucleotide sequence is translated in two different reading frames into two different amino acid sequences. There is a stop codon (TGA) within the coding sequence at base pairs 309–311. Thus, VEGF-B comes in several splicing variants. The 5' end of the cloned cDNA sequence encodes an 102 amino acid long protein with significant homology to the N-terminal domains of VEGF, PlGF and PDGF A and B. In particular, a number of cysteine residues are perfectly conserved within this group of proteins. In addition to the nucleotide sequence (SEQ ID NO:1), FIG. 1 further depicts the deduced amino acid sequence (SEQ ID NO:2) of this first protein.

Translation of the C-terminal end of the cDNA (base pairs 308–475) in a different reading frame results in a protein which is highly homologous to the C-terminal part of $VEGF_{165}$, $VEGF_{189}$ and $VEGF_{206}$. FIG. 2 again shows the nucleotide sequence (SEQ ID NO:1) of FIG. 1, but this time includes the deduced amino acid sequence (SEQ ID NO:3) of the second protein, which is encoded in the second reading frame and is 54 amino acids long. It thus appears that the VEGF-B gene encodes different proteins using alternative splicing of the primary transcript. The last part of the clone, encoding the second peptide might be expressed as a functional protein in other spliced variants of VEGF-B.

The aforedescribed proteins may exist in combined association with an additional N-terminal sequence of approximately five (5) to ten (10) amino acids, as well as a further leader sequence of approximately twenty-one (21) to twenty-eight (28) amino acids. Inasmuch such combined amino acid sequences exhibit the property of promoting the proliferation of endothelial cells and the DNA sequences which code for such combined peptide sequences will hybridize under stringent conditions with the DNA sequence (SEQ ID NO:1) of FIGS. 1 and 2, such amino acid sequences and the DNA which codes for them are expressly contemplated to be within the scope of the present invention.

EXAMPLE 2

Cloning of full length cDNA's for mouse VEGF-B.

Using the approximately 0.9 kb cDNA insert of the previously identified cDNA clone of Example 1 as a probe, an adult mouse heart lambda ZAP-II cDNA library obtained from Stratagene Inc., of La Jolla, Calif. was screened using standard techniques. The library was titrated and plated as recommended and filters were prepared. Following prehybridization at 42° C. in 50 % formamide, 5× SSPE, 5× Denharts solution, 1 % SDS and 100 ug of salmon sperm DNA/ml, the filters were hybridized at the same temperature and in the same solution containing the denatured radiolabelled probe using $10^6$ cpm/ml of hybridization solution. The probe was labelled using a random priming kit (Amersham). After 16 hours the filters were washed in 2× SSC containing 0.5 % SDS for 2×30 mins at 52° C. The filters were exposed overnight using intensifying screens at −70° C. Positive clones were rescreened two times until all plaques on a plate were positive. The inserts were subcloned into the plasmid pBluescript SK+ by in vivo excision as recommended by the supplier.

Several clones were mapped by restriction enzyme analysis and were found to fall into two distinct groups characterized by the length of a Spe1/BamH1 restriction fragment.

The first of these groups comprised three of the restriction mapped clones which each had a 240 bp Spe1/BamH1 restriction fragment. The other group comprised a clone which had a 320 bp Spe1/BamH1 fragment.

The three clones which exhibited the 240 bp Spe1/BamH1 restriction fragment were fully or partially sequenced, and the characteristics of the clones are summarized as follows:

Nucleotide sequence analyses revealed that two of the cDNA clones were substantially identical, although they differed in length, and one has a mutation. One of the clones was full length and contained an open reading frame encoding 188 amino acid residues in which the first 21 amino acids are a clevable signal sequence. The other of the two substantially identical clones terminated at the G of the start initiation codon. It could be inferred by sequence analysis of additional clones that the sequence preceeding the G reads ACCAT. Both of the clones were found to have the same coding region nucleotide sequence, which is depicted in FIG. 3 (SEQ ID NO:4). The deduced amino acid sequence of the open reading frame of the coding region of both of these two cDNA clones is shown in FIG. 4 (SEQ ID NO:5). The resulting protein encoded by this sequence is referred to hereinafter as $VEGF-B_{166}$. In each of the protein names used herein, the subscript number refers to the number of amino acids in the mature protein without the signal sequence.

As would be expected, a comparison of the amino acid sequence encoded by these two clones with the partial amino acid sequence deduced from cDNA clone of Example 1 showed a striking similarity. However, the two open reading frames in the clone of Example 1, each of which encoded an amino acid sequence homologous to a different portion of VEGF, are both present in the same reading frame in each of these two clones according to Example 2. The frame shift in the clone of Example 1 is caused by an insertion of two extra adenine units which displace the C-terminal part of the clone of Example 1 out of frame. The reason for this is not presently understood, but may be due to a cloning artifact.

The coding part of the third clone had a nucleotide sequence identical to those of the preceding two clones except for a 21 bp insertion. FIG. 5 shows the nucleotide sequence of this third clone (SEQ ID NO:6). To facilitate identification, the 21 extra bases are underlined in the Figure. This insertion gives rise to 7 additional amino acid residues in the mature protein. Thus the resulting protein encoded by this longer cDNA is termed $VEGF-B_{173}$. The amino acid sequence of the protein encoded by the cDNA of FIG. 5 is depicted in FIG. 6 (SEQ ID NO:7). The seven additional amino acids also are underlined in the figure for ease of identification. The additional amino acids are inserted into the sequence in a splice site, and sequencing of mouse genomic DNA clones indicates that these additional amino acids are the result of true alternative splicing. Furthermore, based on what is known about the receptor binding site locations of PDGF, the insertion occurs in a position in the protein which is probably part of a receptor binding site. The insertion is thus likely to affect receptor binding and could be of functional importance in influencing antagonist and/or different receptor specificity.

The major portion of the clone of the other group which exhibited a 320 bp Spe1/BamH1 fragment has been found to be identical to the first two clones which exhibited the 240 bp Spe1/BamH1 fragment. The difference is due to the presence of an insertion in the C-terminal part of the sequence, which is clearly a result of alternative splicing.

EXAMPLE 3

Hybrid cDNA clone.

As previously pointed out this original cDNA clone of Example 1 was not full length and may contain an artifact. However, if the extreme 5' nucleotide sequence of the clones which encode VEGF-B$_{166}$ and/or VEGF-B$_{173}$ is added, the open reading frame encodes a protein of 133 amino acids, yielding a mature protein which is 112 amino acids long and hence is named VEGF-B$_{112}$. The hybrid cDNA sequence encoding VEGF-B$_{112}$ is shown in FIG. 7, and the amino acid sequence of the corresponding protein is illustrated in FIG. 8.

FIG. 9 shows an alignment for comparison purposes of the amino acid sequences of Platelet Derived Growth Factor A (PDGF-A) (SEQ ID NO:12), Platelet Derived Growth Factor B (PDGF-B) (SEQ ID NO:13), Placenta Growth Factor (PlGF) (SEQ ID NO:14), Vascular Endothelial Growth Factor (VEGF$_{165}$) (SEQ ID NO:15) and the novel 166 amino acid variant of Vascular Endothelial Growth Factor B of the present invention (VEGF-B$_{166}$) (SEQ ID NO:5), which demonstrates the conserved structure of the growth factors belonging to this family of growth factors. As can be seen from this figure, the homologous relationship of the sequences is apparent, and VEGF-B is a structural homolog of the other growth factors of this group. The boxes in FIG. 9 indicate conserved cysteine residues in the respective protein amino acid sequences. It can be seen that the first eight residues are shared by all members of this family of growth factors, and it is thus evident that all cysteins in the amino terminal part (i.e. the PDGF-like domain) of the proteins are invariant. Furthermore, all the eight of the cysteins in the carboxy terminal part are of VEGF and VEGF-B are shared by both growth factors.

EXAMPLE 4

Cloning of human VEGF-B cDNA.

10$^6$ λ-clones of human fibrosarcoma cDNA library HT1080 in λgt11 (Clontech) were screened with the 0.9 kb insert of the mouse VEGF-B clone pcif 2 according to standard procedures. Among several positive clones, one, termed H.1 was analyzed more carefully and its nucleotide sequence was determined. Based on this sequence two oligonucleotides were designed that would amplify the whole coding region of putative cDNA corresponding to mouse VEGF-B$_{166}$ form.

5'-CACCATGAGCCCTCTGCTCC-3' (forward) (SEQ ID NO:16)

5'-GCCATGTGTCACCTTCGCAG-3' (reverse) (SEQ ID NO:17)

These oligonucleotides were used to amplify by PCR the whole coding region of human VEGF-B corresponding to mouse VEGF-B$_{166}$ from oligo-dT primed human erythroleukemia cell cDNA. The amplified product was cloned into the pCR-vector of TA cloning kit (Invitrogen) and sequenced using standard techniques. The nucleotide sequence of the human VEGF-B cDNA clone is shown in FIG. 10 (SEQ ID NO:10), and the deduced amino acid sequence of human VEGF-B$_{166}$ is shown in FIG. 11 (SEQ ID NO:11).

The amino acid sequences of mouse and human VEGF-B$_{166}$ were aligned as shown in FIG. 12. The putative clevage site for the signal peptidase is indicated by the arrow. Excluding the signal sequences, the mouse and human VEGF-B$_{166}$ amino acid sequences are highly homologous with only 20 replacements out the 166 residues. The replacements are clustered in the N-terminus, in two regions around amino acids 60 and 145. All cysteine residues in both proteins of are invariant. It is notable that the region between residues 66 and 128 is identical apart from one evolutionarily conserved replacements (Q105R). This is of importance since the receptor binding domains are found within this portion of the protein (compared to PDGF structure). From this it can be concluded that it is likely that mouse and human VEGF-B will exhibit cross-reactive binding on the receptor level and thus display identical or similar biological activities. The arrow shows the putative clevage site for the signal peptidase. Vertical bars show identical residues, while stars show amino acid residues which differ between mouse and human VEGF-B$_{166}$.

VEGF-B is synthesized normally in the endoplasmic reticulum of the source cell for subsequent export. Recombinant VEGF-B may be produced by inserting a DNA sequence encoding the VEGF-B protein together with a suitable operatively linked promoter and control sequences into a suitable vector, such as the well known plasmid pBR322 or a derivative thereof, transforming or transfecting a suitable host cell, such as E. coli or a Cos cell, with the resulting vector or other systems well known in the art, screening the resulting transformants or transfectants for VEGF-B expression, and then culturing cell lines or bacterial cell strains which are positive for the expression of VEGF-B. Either a eukaryotic vector or a prokaryotic vector may be used, depending on the type of cell which is to be transfected or transformed therewith.

VEGF-B can be used as a growth factor for populations of endothelial cells in vitro. VEGF-B may be used to promote desirable angiogenesis, i.e. the formation of new blood vessels and capillaries. For example, it may be useful in promoting the development of the corpus luteum and endometrium as an aid to initiating and/or maintaining pregnancy. Administration of VEGF-B may also be useful in supporting embryogenesis, as well as somatic growth and vascular development and differentiation. Topical application of VEGF-B to wounds may be useful in promoting wound healing, and oral administration of VEGF-B may be useful to accelerate the healing of gastric and/or duodenal ulcers.

VEGF-B may exert proliferative effects on mesodermal cells either directly or via improvements in the blood supply.

Tumor assays for VEGF-B may be useful as indicators of metastatic risk. Assays of VEGF-B in body fluids or the tumor itself by histochemistry may be useful as a tumor prognostic factor. Furthermore, because tumor growth requires angiogenesis, administration of VEGF-B may also be useful in promoting tumor growth in laboratory animals in order to test anti-tumorigenic drugs. VEGF-B may also be useful to increase the microvascularity of hypoxic areas of tumors and make them more sensitive to radiation, radiation sensitizing drugs, etc.

The angiogenic action of VEGF-B may be useful in treating ischemic conditions. VEGF-B or agonists could be used to stimulate the development of collateral circulation in cases of arterial and/or venous obstruction, e.g. myocardial infarcts, ischaemic limbs, deep venous thrombisis, and/or postpartum vascular problems.

A VEGF-B/VEGF-B receptor system may be used as an assay system to detect small molecules as agonists/antagonists for development as new drugs. Examples of small molecules which could be detected include, but are not limited to, organic chemicals, peptides, and RNA molecules.

Pharmaceutical compositions may be produced by admixing a pharmaceutically effective amount of VEGF-B protein with one or more suitable carriers or adjuvants such as water, mineral oil, polyethylene glycol, starch, talcum, lactose, thickeners, stabilizers, suspending agents, etc. Such compositions may be in the form of solutions, suspensions, tablets, capsules, creams, salves, ointments, or other conventional forms.

VEGF-B protein also can be used to produce antibodies. Such antibodies may be produced using conventional antibody production techniques. For example, specific monoclonal antibodies may be produced via immunization of fusion proteins obtained by recombinant DNA expression. Labelled monoclonal antibodies, in particular, should be useful in screening for conditions associated with abnormal levels of VEGF-B in the body. For example, assays of VEGF-B levels in blood or urine may be useful as a tumor marker. These monoclonal antibodies to VEGF-B also may be useful in inhibiting angiogenesis associated with high levels of VEGF-B in the body, e.g. in rapidly proliferating, angiogenesis-dependent tumors in mammals, and thereby may retard the growth of such tumors. Treatment may be effected, e.g., by twice weekly intraperitoneal injection of 10 to 500 µg, preferably 50–100 µg of monoclonal antibody. For the therapy of humans, chiaserization or humanization of such monoclonal antibodies is to be preferred.

VEGF-B antagonists such as antibodies may be useful to inhibit new blood vessels in diabetic retinopathy, psoriasis, arthopathies and/or vascular tumors such as haemangiomas.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An isolated protein having the property of promoting proliferation of endothelial cells or mesodermal cells, said isolated protein comprising a sequence of amino acids selected from the group consisting of the amino acid sequence of FIG. 1 (SEQ ID NO:2), the amino acid sequence of FIG. 2 (SEQ ID NO:3), the amino acid sequence of FIG. 4 (SEQ ID NO:5), the amino acid sequence of FIG. 6 (SEQ ID NO:7), the amino acid sequence of FIG. 8 (SEQ ID NO:9), and the amino acid sequence of FIG. 11 (SEQ ID NO:11).

2. An isolated protein according to claim 1, wherein said protein comprises the amino acid sequence of FIG. 1 (SEQ ID NO:2).

3. An isolated protein according to claim 1, wherein said isolated protein comprises the amino acid sequence of FIG. 2 (SEQ ID NO:3).

4. An isolated protein according to claim 1, wherein said isolated protein comprises the amino acid sequence of FIG. 4 (SEQ ID NO:5).

5. An isolated protein according to claim 1, wherein said isolated protein comprises the amino acid sequence of FIG. 6 (SEQ ID NO:7).

6. An isolated protein according to claim 1, wherein said isolated protein comprises the amino acid sequence of FIG. 8 (SEQ ID NO:9).

7. An isolated protein according to claim 1, wherein said isolated protein comprises the amino acid sequence of FIG. 11 (SEQ ID NO:11).

8. An isolated protein according to claim 1, wherein said isolated protein is a mammalian protein.

9. An isolated protein according to claim 8, wherein said mammalian protein is a murine protein.

10. An isolated protein according to claim 8, wherein said mammalian protein is a human protein.

11. An isolated protein according to claim 1, wherein said isolated protein promotes proliferation of vascular endothelial cells.

12. An isolated protein produced by expression of a DNA selected from the group consisting of the DNA of FIGS. 1 and 2 (SEQ ID NO:1), the DNA of FIG. 3 (SEQ ID NO:4), the DNA of FIG. 5 (SEQ ID NO:6), the DNA of FIG. 7 (SEQ ID NO:8), the DNA of FIG. 10 (SEQ ID NO:10), and DNA which hybridizes under stringent conditions with at least one of the foregoing DNA sequences.

13. A pharmaceutical composition comprising an effective endothelial or mesodermal cell proliferation promoting amount of an isolated protein according to claim 1, and at least one pharmaceutical carrier or diluent.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 886 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( F ) TISSUE TYPE: mouse embryo ( v i i ) IMMEDIATE SOURCE:
        ( B ) CLONE: pcif2

( x i ) SEQUENCE DESCRIPTION: SEQ ID NO:1:

```
CGGGACGCCC  AGTGGTGCCA  TGGATAGACG  TTTATGCACG  TGCCACATGC  CAGCCCAGGG      60
AGGTGGTGGT  GCCTCTGAGC  ATGGAACTCA  TGGGCAATGT  GGTCAAACAA  CTAGTGCCCA     120
GCTGTGTGAC  TGTGCAGCGC  TGTGGTGGCT  GCTGCCCTGA  CGATGGCCTG  GAATGTGTGC     180
CCACTGGGCA  ACACCAAGTC  CGAATGCAGA  TCCTCATGAT  CCAGTACCCG  AGCAGTCAGC     240
TGGGGAGAT   GTCCCTGGAA  GAACACAGCC  AATGTGAATG  CAGACCAAAA  AAAAAAGGA      300
GAGTGCTGTG  AAGCCAGACA  GCCCCAGGAT  CCTCTGCCCG  CCTTGCACCC  AGCGCCGTCA     360
ACGCCCTGAC  CCCCGGACCT  GCCGCTGCCG  CTGCAGACGC  CGCCGCTTCC  TCCATTGCCA     420
AGGGCGGGGC  TTAGAGCTCA  ACCCAGACAC  CTGTAGGTGC  CGGAAGCCGC  GAAAGTGACA     480
AGCTGCTTTC  CAGACTCCAC  GGGCCCGGCT  GCTTTTATGG  CCCTGCTTCA  CAGGGACGAA     540
GAGTGGAGCA  CAGGCAAACC  TCCTCAGTCT  GGGAGGTCAC  TGCCCCAGGA  CCTGGACCTT     600
TTAGAGAGCT  CTCTCGCCAT  CTTTTATCTC  CCAGAGCTGC  CATCTAACAA  TTGTCAAGGA     660
ACCTCATGTC  TCACCTCAGG  GGCCAGGGTA  CTCTCTCACT  TAACCACCCT  GGTCAAGTGA     720
GCATCTTCTG  GCTGGCTGTC  TCCCCTCACT  ATGAAAACCC  CAAACTTCTA  CCAATAACGG     780
GATTTGGGTT  CTGTTATGAT  AACTGTGACA  CACACACACA  CTCACACTCT  GATAAAAGAG     840
AACTCTGATA  AAAGAGATGG  AAGACACTAA  AAAAAAAAA   AAAAAA                     886
```

( 2 ) INFORMATION FOR SEQ ID NO:2:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( F ) TISSUE TYPE: mouse embryo ( x i ) SEQUENCE DESCRIPTION: SEQ ID NO:2:

```
Gly Arg Pro Val Val Pro Trp Ile Asp Val Tyr Ala Arg Ala Thr Cys
 1               5                  10                 15

Gln Pro Arg Glu Val Val Pro Leu Ser Met Glu Leu Met Gly Asn
             20              25              30

Val Val Lys Gln Leu Val Pro Ser Cys Val Thr Val Gln Arg Cys Gly
         35              40              45

Gly Cys Cys Pro Asp Asp Gly Leu Glu Cys Val Pro Thr Gly Gln His
     50              55                  60

Gln Val Arg Met Gln Ile Leu Met Ile Gln Tyr Pro Ser Ser Gln Leu
65                  70              75                      80

Gly Glu Met Ser Leu Glu Glu His Ser Gln Cys Glu Cys Arg Pro Lys
             85                  90                  95

Lys Lys Arg Arg Val Leu
            100
```

( 2 ) INFORMATION FOR SEQ ID NO:3:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( F ) TISSUE TYPE: mouse embryo ( x i ) SEQUENCE DESCRIPTION: SEQ ID NO:3:

```
Lys Pro Asp Ser Pro Arg Ile Leu Cys Pro Pro Cys Thr Gln Arg Arg
 1               5                  10                 15

Gln Arg Pro Asp Pro Arg Thr Cys Arg Cys Arg Cys Arg Arg Arg Arg
             20              25              30

Phe Leu His Cys Gln Gly Arg Gly Leu Glu Leu Asn Pro Asp Thr Cys
         35                  40              45

Arg Cys Arg Lys Pro Arg Lys
     50              55
```

( 2 ) INFORMATION FOR SEQ ID NO:4:

( i ) SEQUENCE CHARACTERISTICS:
        ( A ) LENGTH: 565 base pairs
        ( B ) TYPE: nucleic acid
        ( C ) STRANDEDNESS: single
        ( D ) TOPOLOGY: linear ( i i ) MOLECULE TYPE: cDNA -continued (iii) HYPOTHETICAL: NO (vi) ORIGINAL SOURCE:
(F) TISSUE TYPE: adult mouse heart (xi) SEQUENCE DESCRIPTION: SEQ ID NO:4:

| | | | | | |
|---|---|---|---|---|---|
| GAGCCCCCTG | CTCCGTCGCC | TGCTGCTTGT | TGCACTGCTG | CAGCTGGCTC | GCACCCAGGC | 60 |
| CCCTGTGTCC | CAGTTTGATG | GCCCCAGCCA | CCAGAAGAAA | GTGGTGCCAT | GGATAGACGT | 120 |
| TTATGCACGT | GCCACATGCC | AGCCCAGGGA | GGTGGTGGTG | CCTCTGAGCA | TGGAACTCAT | 180 |
| GGGCAATGTG | GTCAAACAAC | TAGTGCCCAG | CTGTGTGACT | GTGCAGCGCT | GTGGTGGCTG | 240 |
| CTGCCCTGAC | GATGGCCTGG | AATGTGTGCC | CACTGGGCAA | CACCAAGTCC | GAATGCAGAT | 300 |
| CCTCATGATC | CAGTACCCGA | GCAGTCAGCT | GGGGGAGATG | TCCCTGGAAG | AACACAGCCA | 360 |
| ATGTGAATGC | AGACCAAAAA | AAAAGGAGAG | TGCTGTGAAG | CCAGACAGCC | CCAGGATCCT | 420 |
| CTGCCCGCCT | TGCACCCAGC | GCCGTCAACG | CCCTGACCCC | CGGACCTGCC | GCTGCCGCTG | 480 |
| CAGACGCCGC | CGCTTCCTCC | ATTGCCAAGG | GCGGGGCTTA | GAGCTCAACC | CAGACACCTG | 540 |
| TAGGTGCCGG | AAGCCGCGAA | AGTGA | | | | 565 |

(2) INFORMATION FOR SEQ ID NO:5:

(i) SEQUENCE CHARACTERISTICS:
(A) LENGTH: 188 amino acids
(B) TYPE: amino acid
(C) STRANDEDNESS: single
(D) TOPOLOGY: linear (ii) MOLECULE TYPE: protein (iii) HYPOTHETICAL: NO (vi) ORIGINAL SOURCE:
(F) TISSUE TYPE: adult mouse heart (xi) SEQUENCE DESCRIPTION: SEQ ID NO:5:

| Met | Ser | Pro | Leu | Leu | Arg | Arg | Leu | Leu | Leu | Val | Ala | Leu | Leu | Gln | Leu |
|---|---|---|---|---|---|---|---|---|---|---|---|---|---|---|---|
| 1 | | | | 5 | | | | | 10 | | | | | 15 | |
| Ala | Arg | Thr | Gln | Ala | Pro | Val | Ser | Gln | Phe | Asp | Gly | Pro | Ser | His | Gln |
| | | | 20 | | | | | 25 | | | | | 30 | | |
| Lys | Lys | Val | Val | Pro | Trp | Ile | Asp | Val | Tyr | Ala | Arg | Ala | Thr | Cys | Gln |
| | | | 35 | | | | 40 | | | | | 45 | | | |
| Pro | Arg | Glu | Val | Val | Val | Pro | Leu | Ser | Met | Glu | Leu | Met | Gly | Asn | Val |
| | | 50 | | | | | 55 | | | | | 60 | | | |
| Val | Lys | Gln | Leu | Val | Pro | Ser | Cys | Val | Thr | Val | Gln | Arg | Cys | Gly | Gly |
| 65 | | | | | 70 | | | | | 75 | | | | | 80 |
| Cys | Cys | Pro | Asp | Asp | Gly | Leu | Glu | Cys | Val | Pro | Thr | Gly | Gln | His | Gln |
| | | | | 85 | | | | | 90 | | | | | 95 | |
| Val | Arg | Met | Gln | Ile | Leu | Met | Ile | Gln | Tyr | Pro | Ser | Ser | Gln | Leu | Gly |
| | | | 100 | | | | | 105 | | | | | 110 | | |
| Glu | Met | Ser | Leu | Glu | Glu | His | Ser | Gln | Cys | Glu | Cys | Arg | Pro | Lys | Lys |
| | | | 115 | | | | | 120 | | | | | 125 | | |
| Lys | Glu | Ser | Ala | Val | Lys | Pro | Asp | Ser | Pro | Arg | Ile | Leu | Cys | Pro | Pro |
| | | | 130 | | | | | 135 | | | | | 140 | | |
| Cys | Thr | Gln | Arg | Arg | Gln | Arg | Pro | Asp | Pro | Arg | Thr | Cys | Arg | Cys | Arg |
| 145 | | | | | 150 | | | | | 155 | | | | | 160 |
| Cys | Arg | Arg | Arg | Arg | Phe | Leu | His | Cys | Gln | Gly | Arg | Gly | Leu | Glu | Leu |
| | | | | | 165 | | | | 170 | | | | | 175 | |
| Asn | Pro | Asp | Thr | Cys | Arg | Cys | Arg | Lys | Pro | Arg | Lys | | | | |
| | | | 180 | | | | | 185 | | | | | | | |

( 2 ) INFORMATION FOR SEQ ID NO:6:

( i ) SEQUENCE CHARACTERISTICS:
        ( A ) LENGTH: 591 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( F ) TISSUE TYPE: adult mouse heart ( x i ) SEQUENCE DESCRIPTION: SEQ ID NO:6:

```
ACCATGAGCC  CCCTGCTCCG  TCGCCTGCTG  CTTGTTGCAC  TGCTGCAGCT  GGCTCGCACC    60
CAGGCCCCTG  TGTCCCAGTT  TGATGGCCCC  AGCCACCAGA  AGAAAGTGGT  GCCATGGATA   120
GACGTTTATG  CACGTGCCAC  ATGCCAGCCC  AGGGAGGTGG  TGGTGCCTCT  GAGCATGGAA   180
CTCATGGGCA  ATGTGGTCAA  ACAACTAGTG  CCCAGCTGTG  TGACTGTGCA  GCGCTGTGGT   240
GGCTGCTGCC  CTGACGATGG  CCTGGAATGT  GTGCCCACTG  GCAACACCA   AGTCCGAATG   300
CAGGTACCAG  GGCCTATGGG  TCAGATCCTC  ATGATCCAGT  ACCCGAGCAG  TCAGCTGGGG   360
GAGATGTCCC  TGGAAGAACA  CAGCCAATGT  GAATGCAGAC  CAAAAAAAAA  GGAGAGTGCT   420
GTGAAGCCAG  ACAGCCCCAG  GATCCTCTGC  CCGCCTTGCA  CCCAGCGCCG  TCAACGCCCT   480
GACCCCCGGA  CCTGCCGCTG  CCGCTGCAGA  CGCCGCCGCT  TCCTCCATTG  CCAAGGGCGG   540
GGCTTAGAGC  TCAACCCAGA  CACCTGTAGG  TGCCGGAAGC  CGCGAAAGTG  A            591
```

( 2 ) INFORMATION FOR SEQ ID NO:7:

( i ) SEQUENCE CHARACTERISTICS:
        ( A ) LENGTH: 195 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( F ) TISSUE TYPE: adult mouse heart ( x i ) SEQUENCE DESCRIPTION: SEQ ID NO:7:

```
Met  Ser  Pro  Leu  Leu  Arg  Arg  Leu  Leu  Leu  Val  Ala  Leu  Leu  Gln  Leu
 1              5                        10                       15

Ala  Arg  Thr  Gln  Ala  Pro  Val  Ser  Gln  Phe  Asp  Gly  Pro  Ser  His  Gln
             20                       25                       30

Lys  Lys  Val  Val  Pro  Trp  Ile  Asp  Val  Tyr  Ala  Arg  Ala  Thr  Cys  Gln
             35                       40                       45

Pro  Arg  Glu  Val  Val  Val  Pro  Leu  Ser  Met  Glu  Leu  Met  Gly  Asn  Val
        50                       55                       60

Val  Lys  Gln  Leu  Val  Pro  Ser  Cys  Val  Thr  Val  Gln  Arg  Cys  Gly  Gly
 65                       70                       75                       80

Cys  Cys  Pro  Asp  Asp  Gly  Leu  Glu  Cys  Val  Pro  Thr  Gly  Gln  His  Gln
                       85                       90                       95

Val  Arg  Met  Gln  Val  Pro  Gly  Pro  Met  Gly  Gln  Ile  Leu  Met  Ile  Gln
                  100                      105                      110

Tyr  Pro  Ser  Ser  Gln  Leu  Gly  Glu  Met  Ser  Leu  Glu  Glu  His  Ser  Gln
             115                      120                      125
```

|     |     |     |     |     |     |     |     |     |     |     |     |     |     |     |
| --- | --- | --- | --- | --- | --- | --- | --- | --- | --- | --- | --- | --- | --- | --- |
| Cys | Glu 130 | Cys | Arg | Pro | Lys 135 | Lys | Lys | Glu | Ser | Ala | Val 140 | Lys | Pro | Asp | Ser |
| Pro 145 | Arg | Ile | Leu | Cys | Pro 150 | Pro | Cys | Thr | Gln | Arg 155 | Arg | Gln | Arg | Pro | Asp 160 |
| Pro | Arg | Thr | Cys | Arg 165 | Cys | Arg | Cys | Arg | Arg 170 | Arg | Arg | Phe | Leu | His 175 | Cys |
| Gln | Gly | Arg | Gly 180 | Leu | Glu | Leu | Asn | Pro 185 | Asp | Thr | Cys | Arg | Cys 190 | Arg | Lys |
| Pro | Arg | Lys 195 |

( 2 ) INFORMATION FOR SEQ ID NO:8:

( i ) SEQUENCE CHARACTERISTICS:
        ( A ) LENGTH: 405 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
ACCATGAGCC CCCTGCTCCG TCGCCTGCTG CTTGTTGCAC TGCTGCAGCT GGCTCGCACC      60
CAGGCCCCTG TGTCCCAGTT TGATGGCCCC AGCCACCAGA AGAAAGTGGT GCCATGGATA     120
GACGTTTATG CACGTGCCAC ATGCCAGCCC AGGGAGGTGG TGGTGCCTCT GAGCATGGAA     180
CTCATGGGCA ATGTGGTCAA ACAACTAGTG CCCAGCTGTG TGACTGTGCA GCGCTGTGGT     240
GGCTGCTGCC CTGACGATGG CCTGGAATGT GTGCCCACTG GCAACACCA  AGTCCGAATG     300
CAGATCCTCA TGATCCAGTA CCCGAGCAGT CAGCTGGGGG AGATGTCCCT GGAAGAACAC     360
AGCCAATGTG AATGCAGACC AAAAAAAAAA AGGAGAGTGC TGTGA                     405
```

( 2 ) INFORMATION FOR SEQ ID NO:9:

( i ) SEQUENCE CHARACTERISTICS:
        ( A ) LENGTH: 133 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

|     |     |     |     |     |     |     |     |     |     |     |     |     |     |     |     |
| --- | --- | --- | --- | --- | --- | --- | --- | --- | --- | --- | --- | --- | --- | --- | --- |
| Met 1 | Ser | Pro | Leu | Leu 5 | Arg | Arg | Leu | Leu | Leu 10 | Val | Ala | Leu | Leu | Gln 15 | Leu |
| Ala | Arg | Thr | Gln 20 | Ala | Pro | Val | Ser | Gln 25 | Phe | Asp | Gly | Pro | Ser 30 | His | Gln |
| Lys | Lys | Val 35 | Val | Pro | Trp | Ile | Asp 40 | Val | Tyr | Ala | Arg | Ala 45 | Thr | Cys | Gln |
| Pro | Arg 50 | Glu | Val | Val | Pro 55 | Leu | Ser | Met | Glu | Leu 60 | Met | Gly | Asn | Val |
| Val 65 | Lys | Gln | Leu | Val | Pro 70 | Ser | Cys | Val | Thr | Val 75 | Gln | Arg | Cys | Gly | Gly 80 |
| Cys | Cys | Pro | Asp | Asp 85 | Gly | Leu | Glu | Cys | Val 90 | Pro | Thr | Gly | Gln | His 95 | Gln |
| Val | Arg | Met | Gln 100 | Ile | Leu | Met | Ile | Gln 105 | Tyr | Pro | Ser | Ser | Gln 110 | Leu | Gly |
| Glu | Met | Ser 115 | Leu | Glu | Glu | His | Ser 120 | Gln | Cys | Glu | Cys | Arg 125 | Pro | Lys | Lys |

Lys Arg Arg Val Leu
          130

( 2 ) INFORMATION FOR SEQ ID NO:10:

( i ) SEQUENCE CHARACTERISTICS:
        ( A ) LENGTH: 570 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( F ) TISSUE TYPE: human fibrosarcoma ( x i ) SEQUENCE DESCRIPTION: SEQ ID NO:10:

| | | | | | |
|---|---|---|---|---|---|
| ACCATGAGCC | CTCTGCTCCG | CCGCCTGCTG | CTCGCCGCAC | TCCTGCAGCT | GGCCCCCGCC | 60 |
| CAGGCCCCTG | TCTCCCAGCC | TGATGCCCCT | GGCCACCAGA | GGAAAGTGGT | GTCATGGATA | 120 |
| GATGTGTATA | CTCGCGCTAC | CTGCCAGCCC | CGGGAGGTGG | TGGTGCCCTT | GACTGTGGAG | 180 |
| CTCATGGGCA | CCGTGGCCAA | ACAGCTGGTG | CCCAGCTGCG | TGACTGTGCA | GCGCTGTGGT | 240 |
| GGCTGCTGCC | CTGACGATGG | CCTGGAGTGT | GTGCCCACTG | GGCAGCACCA | AGTCCGGATG | 300 |
| CAGATCCTCA | TGATCCGGTA | CCCGAGCAGT | CAGCTGGGGG | AGATGTCCCT | GGAAGAACAC | 360 |
| AGCCAGTGTG | AATGCAGACC | TAAAAAAAAG | GACAGTGCTG | TGAAGCCAGA | CAGCCCCAGG | 420 |
| CCCCTCTGCC | CACGCTGCAC | CCAGCACCAC | CAGCGCCCTG | ACCCCCGGAC | CTGCCGCTGC | 480 |
| CGCTGCCGAC | GCCGCAGCTT | CCTCCGTTGC | CAAGGGCGGG | GCTTAGAGCT | CAACCCAGAC | 540 |
| ACCTGCAGGT | GCCGGAAGCT | GCGAAGGTGA | | | | 570 |

( 2 ) INFORMATION FOR SEQ ID NO:11:

( i ) SEQUENCE CHARACTERISTICS:
        ( A ) LENGTH: 188 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( F ) TISSUE TYPE: human fibrosarcoma ( x i ) SEQUENCE DESCRIPTION: SEQ ID NO:11:

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20              25              30

Arg Lys Val Val Ser Trp Ile Asp Val Tyr Thr Arg Ala Thr Cys Gln
        35              40              45

Pro Arg Glu Val Val Val Pro Leu Thr Val Glu Leu Met Gly Thr Val
    50              55              60

Ala Lys Gln Leu Val Pro Ser Cys Val Thr Val Gln Arg Cys Gly Gly
65                  70              75                      80

Cys Cys Pro Asp Asp Gly Leu Glu Cys Val Pro Thr Gly Gln His Gln
                85              90                      95

Val Arg Met Gln Ile Leu Met Ile Arg Tyr Pro Ser Ser Gln Leu Gly
            100             105                 110

|     |     |     |     |     |     |     |     |     |     |     |     |     |     |     |
|---|---|---|---|---|---|---|---|---|---|---|---|---|---|---|
| Glu | Met | Ser<br>115 | Leu | Glu | Glu | His | Ser<br>120 | Gln | Cys | Glu | Cys<br>125 | Arg | Pro | Lys | Lys |
| Lys | Asp<br>130 | Ser | Ala | Val | Lys<br>135 | Pro | Asp | Ser | Pro | Arg<br>140 | Pro | Leu | Cys | Pro | Arg |
| Cys<br>145 | Thr | Gln | His | His | Gln<br>150 | Arg | Pro | Asp | Pro | Arg<br>155 | Thr | Cys | Arg | Cys | Arg<br>160 |
| Cys | Arg | Arg | Arg | Ser<br>165 | Phe | Leu | Arg | Cys | Gln<br>170 | Gly | Arg | Gly | Leu | Glu<br>175 | Leu |
| Asn | Pro | Asp | Thr<br>180 | Cys | Arg | Cys | Arg | Lys<br>185 | Leu | Arg | Arg |

( 2 ) INFORMATION FOR SEQ ID NO:12:

( i ) SEQUENCE CHARACTERISTICS:
        ( A ) LENGTH: 196 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

|     |     |     |     |     |     |     |     |     |     |     |     |     |     |     |     |
|---|---|---|---|---|---|---|---|---|---|---|---|---|---|---|---|
| Met<br>1 | Arg | Thr | Trp | Ala<br>5 | Cys | Leu | Leu | Leu<br>10 | Gly | Cys | Gly | Tyr | Leu<br>15 | Ala |
| His | Ala | Leu | Ala<br>20 | Glu | Glu | Ala | Glu | Ile<br>25 | Pro | Arg | Glu | Leu | Ile<br>30 | Glu | Arg |
| Leu | Ala | Arg<br>35 | Ser | Gln | Ile | His | Ser<br>40 | Ile | Arg | Asp | Leu | Gln<br>45 | Arg | Leu | Leu |
| Glu | Ile<br>50 | Asp | Ser | Val | Gly<br>55 | Ala | Glu | Asp | Ala | Leu<br>60 | Glu | Thr | Ser | Leu | Arg |
| Ala<br>65 | His | Gly | Ser | His<br>70 | Ala | Ile | Asn | His | Val<br>75 | Pro | Glu | Lys | Arg | Pro | Val<br>80 |
| Pro | Ile | Arg | Arg | Lys<br>85 | Arg | Ser | Ile | Glu | Glu<br>90 | Ala | Ile | Pro | Ala | Val<br>95 | Cys |
| Lys | Thr | Arg | Thr<br>100 | Val | Ile | Tyr | Glu | Ile<br>105 | Pro | Arg | Ser | Gln | Val<br>110 | Asp | Pro |
| Thr | Ser | Ala<br>115 | Asn | Phe | Leu | Ile | Trp<br>120 | Pro | Pro | Cys | Val | Glu<br>125 | Val | Lys | Arg |
| Cys | Thr<br>130 | Gly | Cys | Cys | Asn | Thr<br>135 | Ser | Ser | Val | Lys<br>140 | Cys | Gln | Pro | Ser | Arg |
| Val<br>145 | His | His | Arg | Ser | Val<br>150 | Lys | Val | Ala | Lys | Val<br>155 | Glu | Tyr | Val | Arg | Lys<br>160 |
| Lys | Pro | Lys | Leu | Lys<br>165 | Glu | Val | Gln | Val | Arg<br>170 | Leu | Glu | Glu | His | Leu<br>175 | Glu |
| Cys | Ala | Cys | Ala<br>180 | Thr | Ser | Asn | Leu | Asn<br>185 | Pro | Asp | His | Arg | Glu<br>190 | Glu | Glu |
| Thr | Asp | Val | Arg<br>195 |

( 2 ) INFORMATION FOR SEQ ID NO:13:

( i ) SEQUENCE CHARACTERISTICS:
        ( A ) LENGTH: 241 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Met  Asn  Arg  Cys  Trp  Ala  Leu  Phe  Leu  Pro  Leu  Cys  Cys  Tyr  Leu  Arg
 1              5                        10                       15

Leu  Val  Ser  Ala  Glu  Gly  Asp  Pro  Ile  Pro  Glu  Glu  Leu  Tyr  Glu  Met
               20                       25                       30

Leu  Ser  Asp  His  Ser  Ile  Arg  Ser  Phe  Asp  Asp  Leu  Gln  Arg  Leu  Leu
          35                        40                       45

His  Arg  Asp  Ser  Val  Asp  Glu  Asp  Gly  Ala  Glu  Leu  Asp  Leu  Asn  Met
 50                       55                            60

Thr  Arg  Ala  His  Ser  Gly  Val  Glu  Leu  Glu  Ser  Ser  Arg  Gly  Arg
 65                       70                       75                       80

Arg  Ser  Leu  Gly  Ser  Leu  Ala  Ala  Ala  Glu  Pro  Ala  Val  Ile  Ala  Glu
               85                       90                            95

Cys  Lys  Thr  Arg  Thr  Glu  Val  Phe  Gln  Ile  Ser  Arg  Asn  Leu  Ile  Asp
               100                      105                      110

Arg  Thr  Asn  Ala  Asn  Phe  Leu  Val  Trp  Pro  Pro  Cys  Val  Glu  Val  Gln
          115                      120                      125

Arg  Cys  Ser  Gly  Cys  Cys  Asn  Asn  Arg  Asn  Val  Gln  Cys  Arg  Ala  Ser
     130                      135                      140

Gln  Val  Gln  Met  Arg  Pro  Val  Gln  Val  Arg  Lys  Ile  Glu  Ile  Val  Arg
 145                      150                      155                      160

Lys  Lys  Pro  Ile  Phe  Lys  Lys  Ala  Thr  Val  Thr  Leu  Glu  Asp  His  Leu
                    165                      170                      175

Ala  Cys  Lys  Cys  Glu  Thr  Ile  Val  Thr  Pro  Arg  Pro  Val  Thr  Arg  Ser
               180                      185                      190

Pro  Gly  Thr  Ser  Arg  Glu  Gln  Arg  Ala  Lys  Thr  Pro  Gln  Ala  Arg  Val
          195                      200                      205

Thr  Ile  Arg  Thr  Val  Arg  Ile  Arg  Arg  Pro  Pro  Lys  Gly  Lys  His  Arg
     210                      215                      220

Lys  Phe  Lys  His  Thr  His  Asp  Lys  Ala  Ala  Leu  Lys  Glu  Thr  Leu  Gly
 225                      230                      235                      240

Ala
```

( 2 ) INFORMATION FOR SEQ ID NO:14:

( i ) SEQUENCE CHARACTERISTICS:
    ( A ) LENGTH: 149 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:14:

```
Met  Pro  Val  Met  Arg  Leu  Phe  Pro  Cys  Phe  Leu  Gln  Leu  Leu  Ala  Gly
 1              5                        10                       15

Leu  Ala  Leu  Pro  Ala  Val  Pro  Pro  Gln  Gln  Trp  Ala  Leu  Ser  Ala  Gly
               20                       25                       30

Asn  Gly  Ser  Ser  Glu  Val  Glu  Val  Val  Pro  Phe  Gln  Glu  Val  Trp  Gly
          35                       40                       45

Arg  Ser  Tyr  Cys  Arg  Ala  Leu  Glu  Arg  Leu  Val  Asp  Val  Val  Ser  Glu
     50                       55                       60

Tyr  Pro  Ser  Glu  Val  Glu  His  Met  Phe  Ser  Pro  Ser  Cys  Val  Ser  Leu
 65                       70                       75                       80

Leu  Arg  Cys  Thr  Gly  Cys  Cys  Gly  Asp  Glu  Asn  Leu  His  Cys  Val  Pro
               85                       90                            95

Val  Glu  Thr  Ala  Asn  Val  Thr  Met  Gln  Leu  Leu  Lys  Ile  Arg  Ser  Gly
               100                      105                      110
```

```
          Asp  Arg  Pro  Ser  Tyr  Val  Glu  Leu  Thr  Phe  Ser  Gln  His  Val  Arg  Cys
               115                      120                     125

Glu  Cys  Arg  Pro  Leu  Arg  Glu  Lys  Met  Lys  Pro  Glu  Arg  Cys  Gly  Asp
          130                           135                     140

Ala  Val  Pro  Arg  Arg
          145
```

( 2 ) INFORMATION FOR SEQ ID NO:15:

( i ) SEQUENCE CHARACTERISTICS:
        ( A ) LENGTH: 189 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
          Met  Asn  Phe  Leu  Leu  Ser  Trp  Val  His  Trp  Thr  Leu  Ala  Leu  Leu  Leu
          1                   5                        10                      15

Tyr  Leu  His  His  Ala  Lys  Trp  Ser  Gln  Ala  Ala  Pro  Thr  Thr  Glu  Gly
                         20                      25                      30

Glu  Gln  Lys  Ser  His  Glu  Val  Ile  Lys  Phe  Asp  Val  Tyr  Gln  Arg  Ser
                    35                      40                      45

Tyr  Cys  Arg  Pro  Ile  Glu  Thr  Leu  Val  Asp  Ile  Phe  Gln  Glu  Tyr  Pro
               50                      55                      60

Asp  Glu  Ile  Glu  Tyr  Ile  Phe  Lys  Pro  Ser  Cys  Val  Pro  Leu  Met  Arg
          65                      70                      75                      80

Cys  Ala  Gly  Cys  Cys  Asn  Asp  Glu  Ala  Leu  Glu  Cys  Val  Pro  Thr  Ser
                         85                      90                      95

Glu  Ser  Asn  Ile  Thr  Met  Gln  Ile  Met  Arg  Ile  Lys  Pro  His  Gln  Ser
                    100                     105                     110

Gln  His  Ile  Glu  Arg  Met  Ser  Phe  Leu  Gln  His  Ser  Arg  Cys  Glu  Cys
                    115                     120                     125

Arg  Pro  Lys  Lys  Asp  Arg  Thr  Lys  Pro  Glu  Asn  His  Cys  Glu  Pro  Cys
               130                     135                     140

Ser  Glu  Arg  Arg  Lys  His  Leu  Phe  Val  Gln  Asp  Pro  Gln  Thr  Cys  Lys
          145                     150                     155                     160

Cys  Ser  Cys  Lys  Asn  Thr  Asp  Ser  Arg  Cys  Lys  Ala  Arg  Gln  Leu  Glu
                         165                     170                     175

Leu  Asn  Glu  Arg  Thr  Cys  Arg  Cys  Asp  Lys  Pro  Arg  Arg
                         180                     185
```

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CACCATGAGC CCTCTGCTCC                                                                                 20

( 2 ) INFORMATION FOR SEQ ID NO:17:

( i ) SEQUENCE CHARACTERISTICS:
        ( A ) LENGTH: 20 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:17:

GCCATGTGTC ACCTTCGCAG 20